United States Patent [19]

Baughman et al.

[11] Patent Number: 4,646,066
[45] Date of Patent: Feb. 24, 1987

[54] ENVIRONMENTAL INDICATOR DEVICE AND METHOD

[75] Inventors: Ray H. Baughman, Morris Plains; Ronald L. Elsenbaumer, Morristown; Zafar Iqbal, Morristown; Granville G. Miller, Morristown; Helmut Eckhardt, Madison, all of N.J.

[73] Assignee: Allied Corporation, Morris Township, Morris County, N.J.

[21] Appl. No.: 749,326

[22] Filed: Jun. 27, 1985

[51] Int. Cl.[4] .................... G08B 13/18; G08B 21/00
[52] U.S. Cl. ................................. 340/540; 340/584; 340/588; 340/590; 340/600; 340/603; 340/632; 340/665; 340/689; 73/52; 73/336.5; 324/71.1
[58] Field of Search .............. 340/540, 584, 588, 590, 340/600, 602, 603, 632, 665, 689; 73/52, 336.5; 324/71.1

[56] References Cited

U.S. PATENT DOCUMENTS

| | | | |
|---|---|---|---|
| 2,762,035 | 9/1956 | Triman | 340/540 |
| 3,047,847 | 7/1962 | Marsh et al. | 340/540 |
| 3,644,795 | 2/1972 | Taguchi | 340/632 |
| 3,696,679 | 10/1972 | Peterson et al. | 340/590 |
| 3,731,297 | 5/1973 | Dunn, Jr. et al. | 340/540 |
| 4,189,399 | 2/1980 | Patel | 252/408 |
| 4,212,153 | 7/1980 | Kydonieus et al. | 368/62 |
| 4,319,485 | 3/1982 | Terada et al. | 340/584 |
| 4,321,586 | 3/1982 | Cooper et al. | 340/572 |
| 4,325,059 | 4/1982 | Jaye | 340/590 |
| 4,350,978 | 9/1982 | Riccobono | 340/602 |
| 4,426,546 | 1/1984 | Hotta et al. | 340/590 |
| 4,525,704 | 6/1985 | Campbell et al. | 340/632 |
| 4,592,236 | 6/1986 | Battagin et al. | 340/572 |

FOREIGN PATENT DOCUMENTS

0117390 9/1984 European Pat. Off.
2105952 3/1983 United Kingdom.

OTHER PUBLICATIONS

"Small Tags Protect Big Stores," *High Technology*, Aug./Sep., 1983, pp. 16–17.
Baughman, R. H. et al., "Structural Basis for Semiconducting and Metallic Polymer/Dopant Systems," *Chemical Review* 82, pp. 209–222.

*Primary Examiner*—Glen R. Swann, III
*Attorney, Agent, or Firm*—James Riesenfeld

[57] ABSTRACT

A device for monitoring environmental exposure includes an element whose electrical properties change, in a predetermined way, in response to the environmental exposure. The element may be part of a tuned circuit or of a shield for a tuned circuit. In either case, when the tuned circuit is interrogated, preferably by an r.f. or microwave signal, it emits a signal whose intensity depends on the electrical properties of the element. Thus, an incremental environmental exposure can be measured by a change in the signal intensity. The device is particularly useful for monitoring the condition of perishable materials, because it can be located with the perishable inside a packaging material during both storage and interrogation.

46 Claims, 4 Drawing Figures

ENVIRONMENTAL INDICATOR DEVICE AND METHOD

BACKGROUND OF THE INVENTION

1. Field of the Invention

This invention relates to a method of measuring the incremental environmental exposure of an indicator device that includes a tuned circuit and an element that is sensitive to the environmental exposure.

2. Background of the Invention

Several patents have disclosed methods for measuring environmental exposure.

U.S. Pat. No. 4,189,399, issued Feb. 19, 1980, to Patel, discloses co-crystallized acetylenic compounds useful in measuring time-temperature or radiation-dosage history of an article by a color change.

U.S. Pat. No. 4,212,153, issued July 15, 1980, to Kydonieus et al., discloses a two-layer time-temperature indicator that changes color as the interior layer migrates to the outer surface of the exterior layer.

European Patent Application, Publication No. 0117390, published Sept. 5, 1984, discloses a process for measuring environmental exposure of indicator devices that comprise a composition whose optical reflectivity changes incrementally with incremental environmental exposure.

A characteristic of these prior art methods is that the indicator reacts to the environmental exposure with a change in color and/or optical reflectivity. A quantitative measure of the exposure requires an optical detector that can "see" the indicator. Thus, if the indicator is monitoring the exposure of a product, it must be at the surface of the product in order to be read. If the product is packaged, the prior art methods measure the environmental exposure of the outer surface of the packaging, which may be substantially different from the exposure of the product.

SUMMARY OF THE INVENTION

In accordance with the present invention, an indicator device comprises a target that has a tuned electrical circuit and that includes an element having an electrical property that, in response to a particular environmental parameter, changes in a predetermined fashion, whereby the response of the target to an interrogation signal, having a frequency in the microwave range or lower, can be related to the exposure of the target to the parameter. In one embodiment of the invention, the target also comprises an electrical shield, which includes the element and which is positioned so that the response of the target to the interrogation signal depends on the electrical properties of the element.

In operation, an incremental environmental exposure is measured by:

(a) measuring a first response to an interrogation signal of a target that
  (i) comprises a tuned electrical circuit and
  (ii) includes an element having an electrical property that changes in response to the environmental exposure,
(b) measuring a second response, after the incremental environmental exposure of the target, and
(c) calculating the incremental environmental exposure by using a pre-established relationship between the response of the tuned circuit and the environmental exposure.

The devices of the present invention find application in monitoring the exposure of products to environmental parameters, such as temperature, combined time-temperature, humidity, radiation, a particular fluid (gas, vapor or liquid), and mechanical shock.

DETAILED DESCRIPTION OF THE INVENTION

Figure 1:
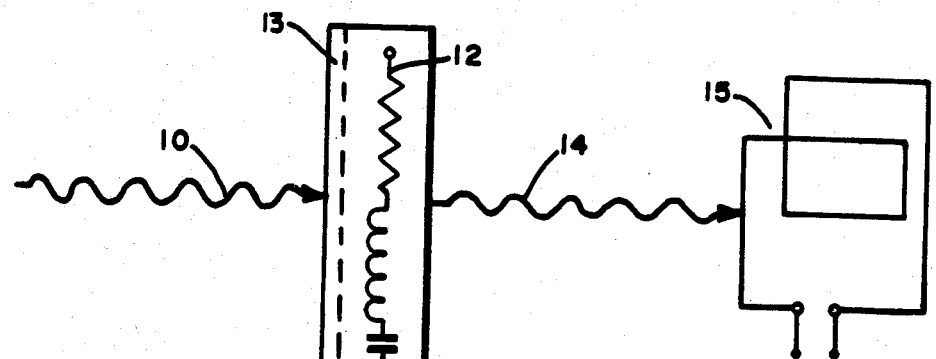
FIG. 1 is a schematic of a system that incorporates a device of the present invention.

This invention provides a method for measuring environmental exposure by making use of an element whose electrical properties change in response to the environmental exposure. The element can be part of a tuned circuit or it can be part of a shield for a tuned circuit. In either case, the tuned circuit is interrogated before and after an incremental environmental exposure, and the change in response can be related to the exposure.

The indicator devices of this invention can operate in either a go, no-go mode or in a quantitative mode. In the go, no-go mode, the devices provide only two responses—a null response or a positive response, depending upon whether or not the environmental exposure has exceeded a specified limit. In the quantitative mode, a continuous change results from increasing exposure to an environmental variable. The devices are particularly useful for monitoring product quality. If the effects of an environmental parameter on both product quality and indicator response are known, a quantitative measure of the effect of the parameter on product quality can be deduced from a measurement of the indicator response. Alternatively, operation in the go, no-go mode can be used to indicate that exposure to an environmental parameter has exceeded a critical value; for example, that the exposure has been sufficient to make the product unusable.

For purposes of this invention, the term "environmental exposure" is to be interpreted broadly to include temperature, time, time-temperature (i.e., the combined effect of the two parameters), humidity, exposure to actinic radiation, mechanical shock, exposure to specified fluids (gases, vapors, or liquids), etc.

The impedance of an electrical circuit depends on its inductance, resistance, and capacitance and on the driving frequency. The current in a passive circuit (i.e., one without an associated power supply) is a maximum when the driving frequency has a particular value, the "resonant frequency," and the circuit may be said to be "tuned" to that frequency. If a target is irradiated with an electromagnetic signal (an "interrogation signal") that includes the resonant frequency, then the presence of the "tuned circuit" in the target can be readily detected by an appropriately situated antenna to yield an output signal. If the target includes, in addition to the tuned circuit, a shield in the path of the interrogation signal, then the resultant output signal depends on the extent of the shielding effect, which, in turn, depends on the electrical conductivity of the shield. If the impedance of the circuit changes, then the resonant frequency changes, and the same incident interrogation signal yields a different response and different output signal.

Thus, any electrical property that affects the circuit impedance can serve as the electrical property whose change, in response to an environmental parameter, underlies this invention. For example, the electrical property can be capacitance, inductance, or conductance (electronic or ionic). Similarly, if a shield is present, a change in its electrical conductivity yields a different response and different output signal, even if the impedance of the tuned circuit remains unchanged. Thus, by interrogating a target repeatedly and monitoring the resultant output signal induced in an antenna, a change in an electrical property of an element of the target can be detected. The element may be a part of a tuned circuit or a shield for a tuned circuit.

Figure 2:
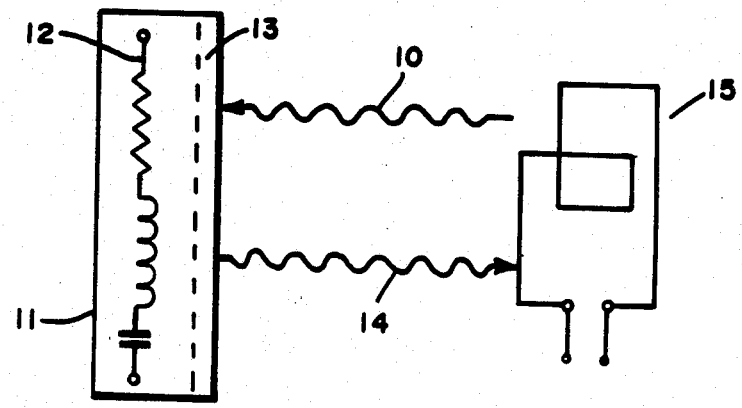
FIG. 2 shows a modification of the system of FIG. 1.

FIG. 1 depicts a schematic of a target of the present invention as it would be used in the method of this invention. Interrogation signal 10, which would typically be in the radio or microwave frequency range, is incident on target 11. Target 11 comprises a tuned circuit 12, which, in one embodiment of the invention, includes an element having an electrical property that changes in response to a particular environmental parameter. In another embodiment, the target includes shield 13. In that embodiment, shield 13 includes an element sensitive to the environmental parameter, but circuit 12 need not. In either case, the signal 14 that emanates from target 11 is converted by an antenna 15 into an electrical current. Preferably, both the source of the interrogation signal 10 and the antenna 15 are in a single instrument package. As is shown in FIG. 2, antenna 15 can be the source of interrogation signal 10.

Tuned circuits of the type suitable for use in this invention have been disclosed in U.S. Pat. No. 4,321,586, issued Mar. 23, 1982, to Cooper et al., and in earlier patents cited there. Cooper et al. used tuned circuits in systems for theft detection, where the concern is merely to distinguish betwen the presence and absence of the tuned circuit. In those systems, the tuned circuit is either removed or totally deactivated, by rupturing a fusible link for example (see U.K. Patent Application No. GB2 105 952 A, published Mar. 30, 1983). These tuned circuits, in the form of antitheft targets, are commercially available. (Suppliers include Checkpoint Systems, Inc., Thorofare, N.J., and Sensormatic Electronics Corp., Deerfield Beach, Fla.) Also available are detection systems, which are used with the targets and which typically respond to the amplitude or frequency of an incident signal. Although the detectors generally operate in the go, no-go mode, they can be readily modified to provide a continuously variable measure of the circuit parameter that is variable. A variety of suitable commercially-available theft-detection devices were disclosed in *High Technology*, pp. 16, 17 (September/October, 1983).

If the element whose electrical properties change is a shield, then a sheet containing that element is situated in the path of the signal from the interrogation system. The shield may be either conducting initially, and made non-conducting, or vice versa. The signal detected decreases as shield conductivity increases.

The signal that is detected in response to interrogation of a target of the present invention depends on the relative locations and orientations of the interrogation source, the target, and the detector. It is important to insure that the "geometry" dependence does not mask the changes that result from environmental exposure of the target. Consequently, if successive measurements are to be made, the relative locations and orientations of the source, target, and detector should remain constant throughout. Alternatively, if in addition to the indicator target, an inert target is used, and the orientation of the two targets relative to each other remains constant, then the response of the "true" indicator target can be inferred from the response of the inert target.

A key to the present invention is identifying an element having an electrical property that changes in response to the particular parameter of interest. A charge-transfer complex whose electrical properties change with time, depending on its temperature, is suitable for use as an element of a time-temperature indicator of the present invention.

Often, it is necessary to incorporate in the target a substance that combines with the element to effect the electrical property change in response to the environmental parameter. The element and substance may be spaced-apart in a matrix through which one of them can diffuse. The matrix may be the same as the element or substance or it may be a third material. Porous paper and plastic film are examples of suitable matrices for time-temperature indicators. The times and temperatures required to reach a specified indicator response level can conveniently be varied by varying the diffusion distance (for example, the thickness of a barrier plastic film) or the porosity of the matrix. Similarly, response characteristics can be varied by choosing matrices having different diffusion coefficients for the substance whose diffusion provides the device response.

When the environmental parameter is the combined effect of time and temperature, a preferred embodiment has an element that is an undoped polymer and a substance that is a dopant vapor. In that case, a suitably chosen polymer may show a large increase in conductivity as the dopant concentration increases (for example, by dopant diffusing through a matrix) with the passage of time. The rate of conductivity increase is generally higher at higher temperatures. Among the polymers that are suitable elements are polymers having conjugated backbones. Polyaniline, polyacetylene, polycarbazoles, polypyrrole, polythiophenes, and polyisothianaphthalene are preferred. Suitable dopants are acceptor dopants such as $AsF_5$, $I_2$, $O_2$, $HCl$, $H_2SO_4$, $FeCl_3$, $SbF_5$, and salts containing $NO^+$, $NO_2^+$ or Fe III and also containing $BF_4^-$, $PF_6^-$, or perchlorate. Other suitable polymers and dopants include those disclosed in R. H. Baughman et al., Chem. Rev. 82, 209 (1982).

In another embodiment of the present invention, the element whose electrical property changes with time-temperature exposure comprises an absorbent substrate, such as paper, and the substance that combines with the element to cause the change is a salt solution.

Salt solutions that are suitable include both inorganic and organic salts in aqueous or nonaqueous solution. Specially preferred are inorganic salts such as alkali or alkaline earth halides in aqueous solution. In general, electrical properties change abruptly at the freezing temperature. The freezing temperature of an aqueous salt solution can be varied from about 0° C. to about −50° C. by varying the salt concentration and the type of salt used. For example, the lower limit can be reached by using aqueous solutions containing about 32 wt. % $CaCl_2$. Other salt/water combinations and concentrations useful for this invention are described in "The Handbook of Chemistry and Physics," 65th edition, pages D-222 to D-274.

A convenient salt form with melting point near room temperature is sodium sulfate decahydrate (m.p. 32° C.), which, admixed with urea, has a melting point of 18°-22° C.

An activatable target of the present invention encapsulates the element or the substance, whose combination causes a change in an electrical property of the element. Preferably, the capsules are microcapsules, with diameters in the range from a few microns to several thousand microns. The preparation of such capsules is described in "Microencapsulation: Processes and Applications," Edited by J. E. Vandegaer, Plenum Press, New York (1974). The use of capsules is particularly convenient for the activation of time-temperature indicator devices to be used at low temperatures, since the activation option eliminates the need to maintain the indicator at low temperatures from the time of manufacture to the time of application. Specifically, rupture of a capsule, mechanically or by freezing, can activate the indicator device by initiating the time-temperature dependent combination of substance and element that results in the electrical property change of the element.

The present invention is suitable for determining exposure to temperature, without regard to time. In such an embodiment, for example, the element may undergo an irreversible change in an electrical property at a particular temperature. Depending on the range of temperatures to be monitored and the particular application, the particular temperature may mark either a lower limit (freezing, for example) or an upper limit (melting, for example).

A salt deposited on filter paper impregnated with frozen water can be used to show that a product has warmed above the ice point. The salt should not be very hygroscopic and should dissolve in water formed by melting at the upper temperature to cause an irreversible change in an electrical property.

A particularly convenient type of indicator for demulsification resulting from freezing (freeze indicator) uses the product to be monitored as the element. For example, if the element comprises salad dressing or a similar emulsion, demulsification can cause the electrical property change that is detected.

Polymer/dopant systems, discussed above, can serve as fluid sensors; i.e., sensors for gases, vapors, and liquids. For example, alkali-metal doped polyacetylene or alkali-metal doped poly(p-phenylene) provide the basis for very sensitive integrating devices for the detection of trace oxygen or water vapor. Less sensitive elements for the detection of oxygen can be made from acceptor-doped polymers, such as acceptor-doped polyacetylene.

Doped or undoped conjugated polymers can be used to detect the release of toxic donor or acceptor chemicals either by the formation or the destruction of conducting charge transfer complexes as a consequence of exposure to these chemicals. For example, doped or undoped polyacetylene can provide the element for a detector for iodine, ammonia, sulfuric acid, $H_2S$, hydrazine, $SO_2$, and the like.

Humidity is another environmental parameter that can be monitored by the present invention. One technique uses an element comprising a moisture-sensitive, highly-conducting charge-transfer complex, such as a doped polymer. However, the preferred element comprises a deliquescent salt deposited on a porous substrate, such as filter paper. To increase the sensitivity of such a device, one would go from less deliquescent to more deliquescent salts. A preferred salt for use in the element of a humidity indicator is $CaCl_2$. Depending upon the choice of element, the humidity indicator can be either integrating or nonintegrating. For example, the use of a very deliquescent salt protected by a polymer membrane that is semipermeable to water can provide an integrating humidity indicator, since a very hydroscopic salt will not lose its hydration in the application temperature range. By selecting a salt of suitable deliquescence and the optional use of semipermeable moisture barriers of selected polymer type and thickness, the response of the element can be made to replicate the effect of humidity on the quality of a product. Depending upon the device construction, humidity response will depend on temperature to a greater or lesser extent, since diffusion and hydration processes generally depend upon temperature. Analogous dependence on the combined effects of humidity and temperature are found for many products, such as tobacco products.

Exposure to actinic radiation can be measured by the device and method of the present invention. For that purpose, the element may be a polymer that includes a photochemical that generates a dopant for the polymer on exposure to the radiation. The dopant causes a large increase in the electrical conductivity of the polymer.

Suitable polymers are, for example, poly(p-phenylene), polyacetylene, poly(p-phenylene sulfide), poly(p-phenyl vinylene), polyaniline, polypyrrole, polycarbazoles, polythiophene, and polymeric sulfur nitride.

Suitable photochemicals include triarylselenonium salts, triarylsulfonium salts, and diaryliodium salts of the form:

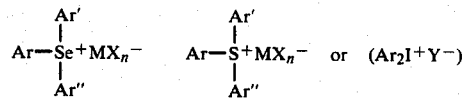

where $MX_n^-$ is $BF_4^-$, $PF_6^-$, $SbF_6^-$, etc, $Y^-$ is $Cl^-$, $Br^-$, $I^-$, or $MX^-_n$, and where Ar, Ar', and Ar" are phenyl or substituted phenyl, (see "Photoinitiated Cationic Polymerization by Triarylselenonium Salts," J. V. Crivello and J. H. W. Lam, Journal of Polymer Science: Polymer Chemistry Edition Vol. 17, 1047–1057 (1979)). Halocarbon acceptors, such as $CCl_4$, $CBr_4$, and $CI_4$, are other suitable photochemicals (see D. C. Hofer et al., Appl. Phys. Lett. 37, 314–316 (1980)).

The principal restriction on the combination of particular photochemicals and polymers is that the dopant generated by the radiation must have sufficient electron affinity or the polymer have sufficiently low ionization potential so that charge carriers are generated in the polymer when the two combine. For example, iodine is a good choice for polyacetylene, but not for poly(p-phenylene sulfide), because iodine has relatively low electron affinity, and the ionization potential of poly(p-phenylene sulfide) is much higher than that of polyacetylene.

Generally, the conductivity change that provides the device response need not result from the doping of a polymer, but can instead arise from the formation of a conducting charge-transfer complex. An example is the ionization of tetrathiafulvalene by bromine to produce a highly-conducting charge-transfer complex. In this case the element whose electrical property changes comprises tetrathiafulvalene and the substance that combines with the element is bromine, generated when $CBr_4$ is exposed to actinic radiation. Also, the radiation-sensitive chemical can produce a compensating agent that reacts with a dopant that is already part of a conducting charge-transfer complex. The reaction of the radiation-generated compensating agent with the dopant initially in the charge-transfer complex (e.g., reaction of electron donor with an electron acceptor doping agent) can lead to a decrease of electrical conductivity.

Suitable actinic radiation includes γ-rays, x-rays, electrons and other particle beams (proton, alpha particles, etc.), and ultraviolet and visible light. A particular photochemical may be used to monitor more than one of these types of radiation; thus, if the effect of a single type is to be monitored, it is sometimes necessary to mask the target from the extraneous types.

It is often important to know whether an article has been subjected to mechanical shock, and the present invention provides a device and method for determining that. When the environmental parameter being monitored is mechanical shock, the device preferably comprises an element and a substance that can combine with the element (as a result of mechanical shock) to change the electrical property. The element may comprise a conjugated polymer, such as polyacetylene, and the substance may comprise a solution that can cause a large increase in polymer conductivity, such as an aqueous solution of $KI_3$. Alternatively, the element can comprise a salt dispersed on filter paper and the substance a solvent for the salt. In a preferred embodiment, the element comprises absorbent paper and the substance is a salt solution contained in a frangible capsule.

Capsules suitable for the present invention may be of glass, polymer, thin metal foil, etc., and may include means for breaking the capsule by mechanical shock, such as a ball bearing within the capsule. Alternatively, the capsule may be sandwiched near the pivot point of a movable lever. The sensitivity of the indicator device to mechanical shock can be controlled by varying the mechanical strength of the capsule (changing wall thickness and/or the mechanical properties of the capsule material) and, for example, changing the weight and size of the ball bearing. Capsule size is preferably in the range of about 1 $mm^3$–1 $cm^3$ volume.

Indicator devices that denote that a shipping package has not been held right-side-up during shipping can be constructed analogously to the mechanical shock indicators, except that instead of a liquid being released by breaking a capsule, the liquid pours out of a tilted holder.

The devices of the present invention find their primary application in monitoring the environmental exposure to which a product has been subjected and/or its effect on the product. That purpose may be accomplished by first attaching a device of this invention to the product and then determining the exposure to which the product has been subjected from a calculation of the exposure to which the device has been subjected. The device (and product) may be in a sealed package and can be interrogated without opening the package. Of course, the packaging material must not interfere with the interrogation. Prior art devices, on the other hand, generally must be located at the surface of the package.

The following examples are presented in order to provide a more complete understanding of the invention. The specific techniques, conditions, materials, and reported data set forth to illustrate the principles and practices of the invention are exemplary and should not be construed as limiting the scope of the invention.

EXAMPLE 1

Time-temperature indicator

Approximately 80% of one side of an rf-antitheft target (38 mm×38 mm in size, from Check Point Systems, Inc., Thorofare, N.J.), which operates at a resonance frequency of 8.2 MHz, was covered with a piece of undoped 0.1–0.2 mm polyacetylene film (prepared by the method of Ito, Shirakawa, and Ikeda, J. Polym. Sci., 12, 11 (1974)).

The laminated target was then encapsulated in a polyethylene case under argon together with 200 μl of an aqueous $KI_3$ solution in a breakable capsule. When interrogated with a signal at or near the resonance frequency, the target emitted a signal that was detected as 7.5 V on a conventional radio-frequency detector 6 cm from the target.

Figure 3:
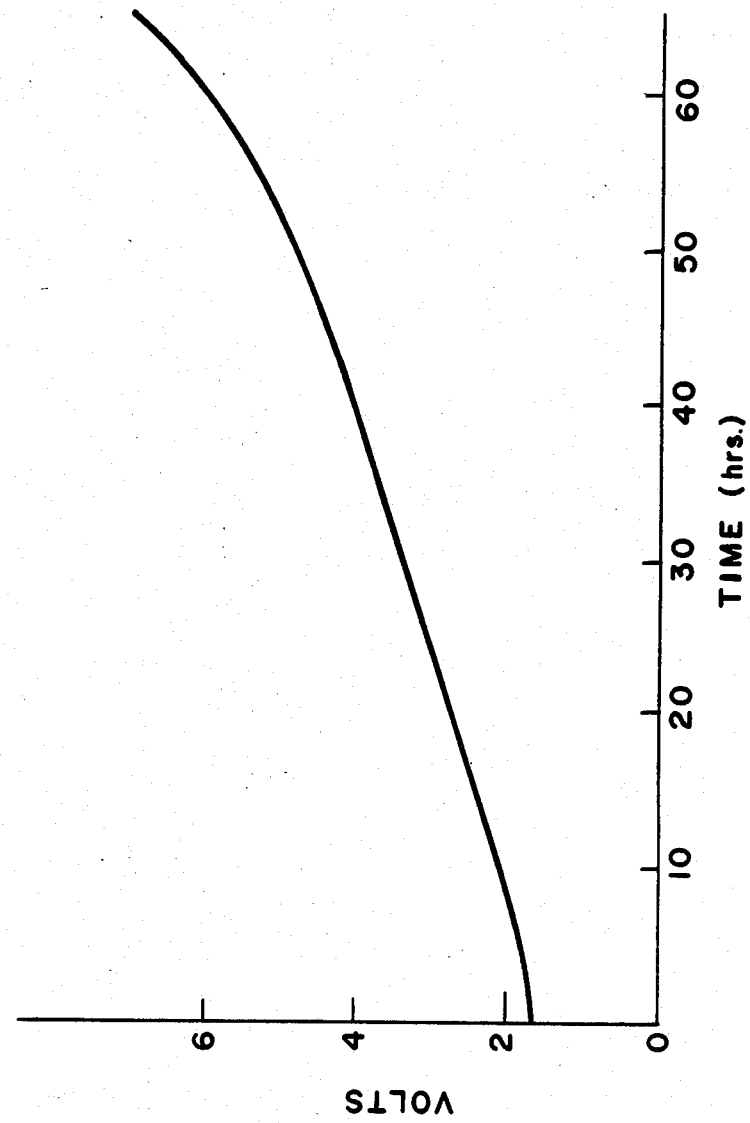
FIG. 3 is a graph of the response of a time-temperature indicator of the present invention.

The device was then activated by breaking the capsule, allowing the solution to dope the polyacetylene to a conductivity of 100–400 S/cm. At this point the interrogated target provided a reading of 1.8 V on the detector. This voltage gradually increased with time as oxygen diffused through the polyethylene case and degraded the conductivity of the doped polyacetylene. To accelerate the degradation process, the polyethylene case was punctured, and the voltage response of the target in ambient was monitored over a period of a few days. The voltage increased slowly (as shown in FIG. 3) as the conductivity of the polyacetylene decayed. Similar results are achieved with the degradation of other polymers.

EXAMPLE 2

Time-temperature indicator

Figure 4:
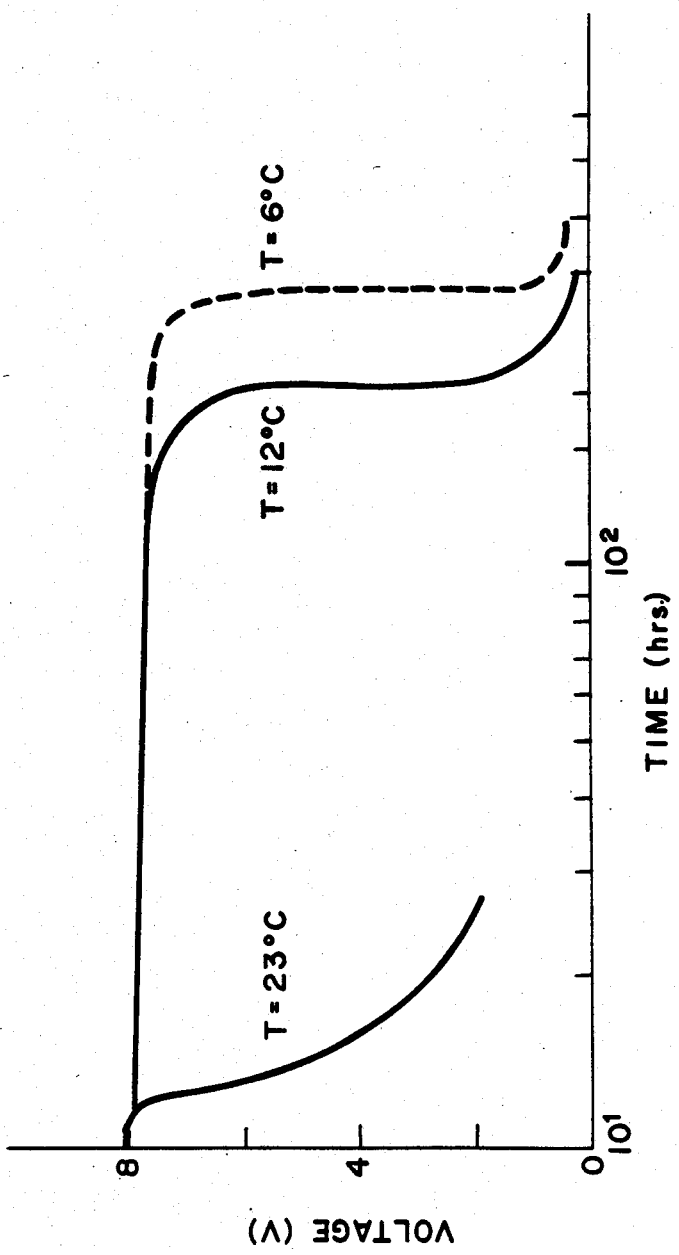
FIG. 4 is a graph of the response of another time-temperature indicator of the present invention.

A target like the one used in Example 1 was covered on one side with a filter paper coated with dry $CaCl_2$ and the composite was sealed in polyethylene. At this point the response of the modified target was identical to that of an unmodified target in the sense that both targets provided identical readings on a detector 6 cm away. A small area of polyethylene covering the filter paper side of the target was punctured with holes over which a film of cellulose acetate butyrate was cast. This modified device was sealed inside another polyethylene container containing a piece of wet filter paper. The target response abruptly dropped to zero after water vapor diffused through the cellulose film and dissolved the $CaCl_2$ to form an ionically-conducting solution in the filter paper. The onset of change in target response, as well as the duration of the initial delay time, depends on the rate of diffusion of water vapor through the barrier film (cellulose in this case), which is a function of temperature. Voltage vs time profiles for devices constructed as above and held at 6°, 12°, and 23° C. are shown in FIG. 4.

EXAMPLE 3

Time-temperature indicator

A coating of conductive polyaniline doped with HCl was applied to one surface of a target like the one described in Example 1. The target at this point is nearly "invisible" to the detector at a distance of 6 cm. Exposure of the target to temperatures in excess of 100°–125° C. for short times causes the target response to increase, where the extent of signal increase depends on both the exposure time and the temperature. The thermal treatment above these temperatures causes vaporization of the dopant, resulting in gradual de-doping and conductivity loss of the polyaniline coating.

EXAMPLE 4

Freeze/thaw indicator

One surface of a target similar to the one described in Example 1 was covered with a piece of filter paper soaked in an aqueous solution containing 1% by wt. of NaCl (specific conductance of 16 mS/cm) and the whole device was encapsulated to prevent water evaporation. The target was completely "invisible" as evidenced by a zero reading on the detector. On cooling to below about $-0.6°$ C., the aqueous solution froze and the target became completely "visible" (7.5 V reading on the detector). On rewarming, the solid phase became fluid again and the target returned to the "invisible" state (zero reading). This demonstrates a reversible freeze/thaw indicator useful for signaling the freezing of items containing water.

Besides aqueous solutions, other liquid/ionically-conductive material combinations with vastly different freezing points are possible (e.g., sulfuric acid, (m.p. 10° C.), phosphoric acid (m.p. 29° C.), acetic acid (m.p. 16.6° C.), acetonitrile/LiAsF$_6$ (m.p. $-45°$ C. and below), sulfolane/Li$^+$CF$_3$SO$_3^-$ (m.p. 28° C. and below), etc.), providing a large family of indicator devices useful over a wide range of temperatures.

EXAMPLE 5

Freeze indicator

Microcapsules containing an aqueous NaCl solution were coated on a piece of filter paper. The coated filter paper was placed on one surface of a target like the one described in Example 1. At this point the target was completely "visible" (7.5 V reading at a distance of 6 cm from the receiver). The target remained visible on cooling to below the freezing point of the aqueous solution. On rewarming above the thaw-point, the target became "invisible" (zero volt reading, 6 cm from the receiver). On freezing, the microcapsules ruptured due to expansion of the aqueous phase. On thawing, an ionically-conductive solution formed in the filter paper and caused the attenuation of target response. Thus, a target invisible at room temperature indicates that it was subjected to temperatures low enough to freeze the solution inside the microcapsules. As in Example 4, the low-temperature limit can be selected by proper choice of salt, solvent, and concentration.

EXAMPLE 6

γ-radiation dosage indicator

Undoped non-conductive polyaniline powder (prepared by the method of A. G. Green et al., J. Chem. Sci. 97, 2388-2403 (1910)) in a poly(vinylchloride) matrix was applied to one side of a target like the one used in Example 1. At this point, the target was completely "visible" as evidenced by a reading of 7.5 V on the detector held 6 cm from the target. The target was irradiated with γ-rays from a cobalt-60 source at a rate of 1 M rad/hr for 100 hr. The target response (voltage) was reduced by 20% as a consequence of this radiation dosage, perhaps because irradiation of the poly (vinylchloride) released HCl, which doped the polyaniline to a conducting state.

EXAMPLE 7

UV dosimeter

A thin coating of tetrathiafulvalene (TTF) (Aldrich Chem. Co.) wetted with CCl$_4$ was applied to one side of a target identical to the one described in Example 1. At this point the target response was the same as the unmodified target (100% active). On exposing the modified target to UV radiation (256 and 366 nm, $\sim$300 μW), the target response slowly diminished. After an exposure time of 70 min., the signal strength decreased by 30%.

A similar device was fabricated using polyacetylene as the dynamic element in the target.

A large LC coil used for antitheft detection and supplied by Checkpoint Systems Inc., was modified by incorporating a piece of undoped polyacetylene film (initial conductivity of $10^{-7}$ S/cm, 5 mm $\times \sim$10 mm $\times$ 0.13 mm) in parallel with the circuit (contacts were made using Electrodag ® conductive cement).

The undoped polyacetylene film was covered with a saturated solution of Ph$_2$I$^+$PF$_6^-$ in CH$_2$Cl$_2$. After evaporation of the CH$_2$Cl$_2$, the coil was encapsulated in polyethylene under argon. At this point, the modified target provided the same response as an unmodified antitheft target (100% active). After the polyacetylene was irradiated with UV light at 254 nm for 60 min., the target response decreased by 85%. Here, the UV irradiation presumably produces HPF$_6$, which subsequently dopes the polyacetylene, thereby rendering the polymer conductive.

EXAMPLE 8

Gas/vapor sensor

Undoped polyaniline (conductivity $<10^{-7}$ S/cm) was applied as a powder to one side of an rf target like the one described in Example 1. The target remained 100% active. On exposure to HCl vapor, the target response rapidly dropped to 15% of its original value. The response remained constant when the target was removed from the HCl vapors indicating that the response is permanent.

EXAMPLE 9

Gas/vapor sensor

A coating of doped and conductive polyaniline was applied to one side of a target like the one described in Example 1. At this point, the target was nearly "invisible" at a distance of 6 cm. On exposure to ammonia vapor, the target response rapidly increased, finally giving a value of $\sim$6 V on the detector. Removing the target from the ammonia vapors caused no change in target response, indicating that a permanent change occurred. This demonstrates that such a modified target can function as a sensor for the release of reducing agents.

EXAMPLE 10

Gas sensor

A 38 mm square of 0.25 mm thick polyacetylene film was wetted with a degassed 48% aqueous HBF$_4$ solution and placed on one side of a target of the type described in Example 1. The target registered a 6.8 V reading on the receiver at a distance of 5.5 cm. On exposure to atmospheric oxygen, the reading gradually decreased to a limiting value of 4.0 V after 2 days. The target response results from gradual oxygen doping of the polyacetylene film. A slower rate of response can be achieved by encapsulating the target; e.g., in a polyethylene case.

EXAMPLE 11

Humidity detector

One surface of an rf target similar to the one described in Example 1 was coated with dry $CaCl_2$ on a porous substrate and the whole encapsulated in a polyethylene pouch with a number of holes. This device is completely "visible" to the detector. However, when the total exposure to environmental humidity exceeds a certain limiting value, the coating absorbs sufficient $H_2O$ such that it goes into solution and makes the device "invisible" to the detector. This type of device functions as an integrating humidity indicator.

We claim:

1. An indicator device comprising a target that has a tuned electrical circuit and that includes an element having an electrical property that, in response to a particular environmental parameter, changes in a predetermined fashion, whereby the response of the target to an electromagnetic interrogation signal, having a frequency in the microwave range or lower, can be related to the exposure of the target to the parameter.

2. The device of claim 1 in which the tuned electrical circuit is in proximity to an electrical shield that includes the element.

3. The device of claim 1 in which the element comprises a charge-transfer complex.

4. The device of claim 1 further comprising a substance that can combine with the element to cause the change in the electrical property.

5. The device of claim 1 in which the environmental parameter is time-temperature.

6. The device of claim 5 in which the element comprises a charge-transfer complex.

7. The device of claim 5 further comprising a substance that can combine with the element to cause the change in the electrical property.

8. The device of claim 7 in which the element and the substance are spaced apart in a matrix through which at least one of them can diffuse.

9. The device of claim 7 in which the element is an undoped polymer and the substance is a dopant vapor.

10. The device of claim 1 in which the environmental parameter is temperature.

11. The device of claim 10 in which the electrical property changes irreversibly when the element reaches one or more predetermined temperatures.

12. The device of claim 10 in which the element is a low-melting dielectric solid having a melting point or glass transition point below 100° C.

13. The device of claim 10 in which the element comprises an emulsion that demulsifies on freezing.

14. The device of claim 10 further comprising a substance that can combine with the element to cause the change in the electrical property.

15. The device of claim 14 in which the element comprises an absorbent substrate and the substance is a salt solution contained in a temperature-sensitive frangible capsule.

16. The device of claim 1 in which the environmental parameter is humidity.

17. The device of claim 16 in which the element is a moisture-sensitive conducting polymer.

18. The device of claim 16 in which the element is a moisture-sensitive salt on an absorbent substrate.

19. The device of claim 1 in which the environmental parameter is actinic radiation.

20. The device of claim 19 in which the element is a polymer that includes a chemical that generates a dopant for the polymer on exposure to actinic radiation.

21. The device of claim 1 in which the environmental parameter is mechanical shock.

22. The device of claim 21 further comprising a substance than can combine with the element to cause the change in the electrical property.

23. The device of claim 22 in which the element comprises an absorbent substrate and the substance is a salt solution contained in a frangible capsule.

24. A method of measuring an incremental exposure to an environmental parameter comprising
  (a) measuring a first response to an electromagnetic interrogation signal of a target that
    (i) comprises a tuned electrical circuit and
    (ii) includes an element having an electrical property that changes in response to the exposure,
  (b) measuring a second response, after the incremental environmental exposure of the target, and
  (c) calculating the incremental environmental exposure by using a predetermined relationship between the response of the tuned circuit and the environmental exposure.

25. A method of determining the effect of an incremental environmental exposure on a product, which comprises measuring, by the method of claim 24, the incremental environmental exposure of an indicator device affixed to the product and calculating, using a predetermined relationship, the effect on the product from the exposure of the device.

26. The method of claim 25 in which the product and indicator device are enclosed in a package and the interrogation signal emanates from outside the package.

27. The method of claim 24 in which the environmental parameter is time-temperature.

28. The method of claim 27 further comprising a substance that can combine with the element to cause the change in the electrical property.

29. The method of claim 28 in which the element and the substance are spaced apart in a matrix through which at least one of them can diffuse.

30. The method of claim 28 in which the element is an undoped polymer and the substance is a dopant vapor.

31. The method of claim 28 in which the element comprises an absorbent substrate and the substance is a salt solution contained in a temperature-sensitive frangible capsule.

32. The method of claim 24 in which the environmental parameter is temperature.

33. The method of claim 32 in which the electrical property changes irreversibly when the element reaches a predetermined temperature.

34. The method of claim 33 in which the element is a dielectric solid having a melting point or glass transition point below 100° C.

35. The method of claim 32 further comprising a substance that can combine with the element to cause the change in the electrical property.

36. The method of claim 35 in which the element comprises an absorbent substrate and the substance is a salt solution contained in a temperature-sensitive frangible capsule.

37. The method of claim 24 in which the environmental parameter is relative humidity.

38. The method of claim 37 in which the element is a moisture-sensitive salt on an absorbent substrate.

39. The method of claim 37 in which the element is a moisture-sensitive conducting polymer.

40. The method of claim 24 in which the environmental parameter is ionizing radiation.

41. The method of claim 40 in which the element is a polymer that includes a chemical that generates a dopant for the polymer on exposure to ionizing radiation.

42. The method of claim 24 in which the environmental parameter is mechanical shock.

43. The method of claim 42 further comprising a substance that can combine with the element to cause the change in the electrical property.

44. The method of claim 43 in which the element comprises an absorbent substrate and the substance is a salt solution contained in a frangible capsule.

45. The method of claim 24 in which the environmental parameter is an atmosphere that includes a particular fluid.

46. The method of claim 45 in which the fluid comprises oxygen.

* * * * *